(12) United States Patent
Maire

(10) Patent No.: US 7,201,741 B2
(45) Date of Patent: Apr. 10, 2007

(54) DEVICE AND METHOD FOR DOSING SUBSTANCES

(75) Inventor: Bruno Maire, Oberburg (CH)

(73) Assignee: TecPharma Licensing AG, Burgdorf (CH)

(*) Notice: Subject to any disclaimer, the term of this patent is extended or adjusted under 35 U.S.C. 154(b) by 30 days.

(21) Appl. No.: 10/360,190

(22) Filed: Feb. 7, 2003

(65) Prior Publication Data

US 2003/0130853 A1 Jul. 10, 2003

Related U.S. Application Data

(63) Continuation of application No. PCT/CH01/00470, filed on Jul. 31, 2001.

(30) Foreign Application Priority Data

Aug. 9, 2000 (DE) .................. 100 38 936

(51) Int. Cl.
*A61M 5/00* (2006.01)

(52) U.S. Cl. .................. 604/208; 604/154; 368/10; 700/242; 704/275; 704/258

(58) Field of Classification Search ........ 704/270–278, 704/258; 604/208, 154; 454/157; 368/10; 222/1; 700/242
See application file for complete search history.

(56) References Cited

U.S. PATENT DOCUMENTS

| | | | | |
|---|---|---|---|---|
| 4,950,246 A | * | 8/1990 | Muller | 604/154 |
| 5,221,025 A | * | 6/1993 | Privas | 222/1 |
| 5,383,865 A | | 1/1995 | Michel | |
| 5,812,064 A | * | 9/1998 | Barbour | 340/5.91 |
| 5,835,455 A | * | 11/1998 | Hanson et al. | 368/10 |
| 5,928,201 A | | 7/1999 | Poulsen et al. | |
| 5,961,487 A | | 10/1999 | Davis | |
| 6,264,548 B1 | * | 7/2001 | Payne et al. | 454/157 |
| 6,332,100 B1 | * | 12/2001 | Sahai et al. | 700/242 |
| 6,340,357 B1 | * | 1/2002 | Poulsen et al. | 604/208 |

FOREIGN PATENT DOCUMENTS

DE 198 20 316 A1 11/1999
EP 0 293 958 A1 7/1988

* cited by examiner

Primary Examiner—Vijay B. Chawan
(74) Attorney, Agent, or Firm—Dorsey & Whitney LLP

(57) ABSTRACT

The invention relates to a device for dosing substances to be dispensed, in particular medicinal liquids, in particular for an injection, the device including a setting device for setting the amount of the substance to be dispensed, a signal receiving device for detecting setting signals of the setting device, an evaluation unit for receiving and evaluating the setting signals detected by the signal receiving device, a device for generating speech signals in accordance with the evaluation signals of the evaluation unit, and a device for outputting speech signals. The invention encompasses a method for dosing substances to be dispensed including the steps of detecting a setting signal of a setting device and outputting a speech signal in accordance with the setting signal detected.

29 Claims, 1 Drawing Sheet

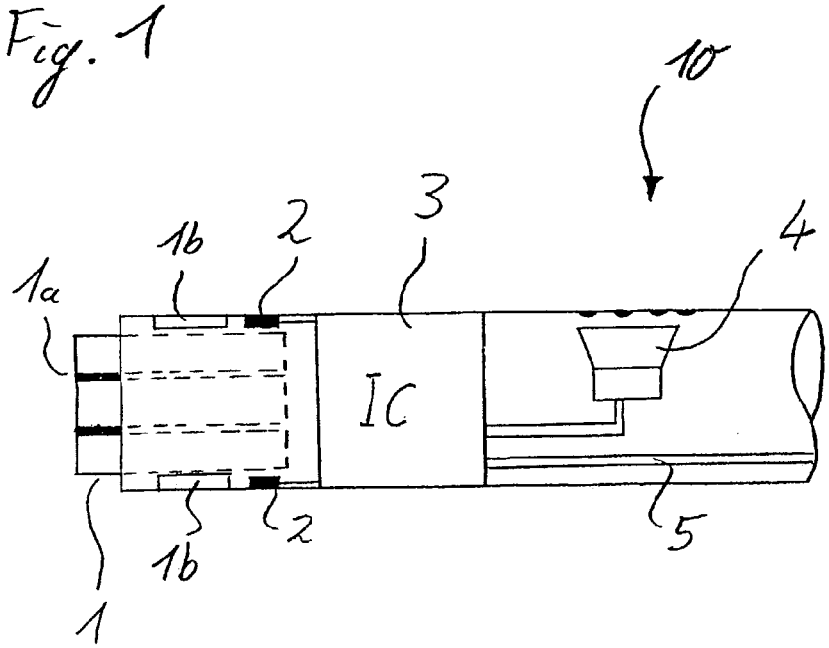
Figure 2
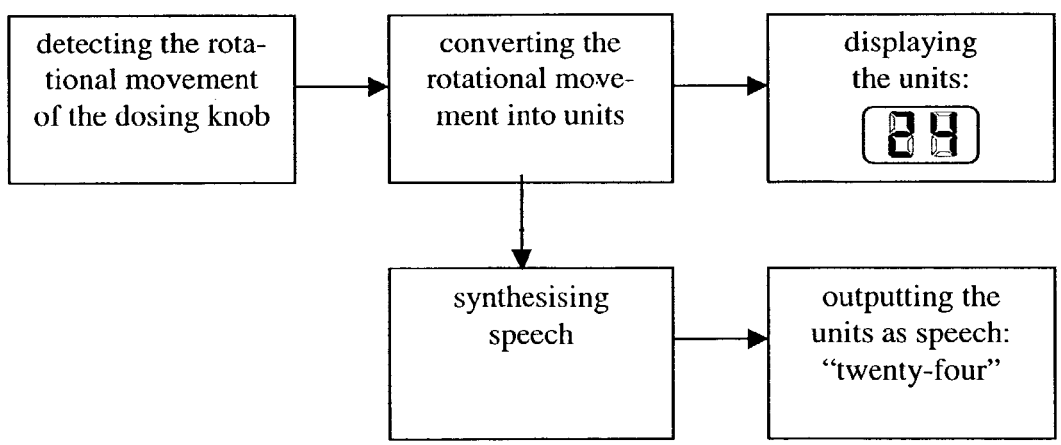

DEVICE AND METHOD FOR DOSING SUBSTANCES

CROSS-REFERENCE TO RELATED APPLICATIONS

This application is a continuation of International Patent Application No. PCT/CH01/00470, filed on Jul. 31, 2001, which claims priority to German Patent Application No. 100 38 936.8, filed on Aug. 9, 2000, both of which are incorporated herein by reference.

BACKGROUND

The present invention relates to devices and methods for dosing, or measuring and delivering, substances to be dispensed. More particularly it relates to devices and methods for dosing liquids, including medicinal liquids such as insulin-containing liquids, which has to be reliably performed.

A display means for a medical injection device is known from EP 0 581 925 B1, in which the amount of an injection dose to be injected can be set by means of a rotatable operating knob and the number of defined partial rotations of the operating knob is shown on an LCD display.

DE 198 20 316 A1 discloses a processor-controlled hand-held device for accommodating conventional injection syringes and ampoules, comprising an acoustic display device for set and dispensed amount parameters, wherein a particular amount is output as speech or a signal, only once, or after, said amount has been set.

So-called "speaking thermometers" for the visually impaired and blind are known from DE 297 15 973 U1 and DE 299 01 739 U1, which, at the end of a measuring process, output a measured temperature acoustically.

A general device for generating a speech output once a measurement has been taken is known from GB 2 049 189 A.

SUMMARY

It is the object of the present invention to provide a device and a method for dosing substances to be dispensed, which make the process of setting the dose or amount to be dispensed easier for the user.

This object is addressed by a device for dosing substances to be dispensed, in particular liquids, in particular for an injection, comprising: a setting device for setting the amount of the substance to be dispensed; a signal receiving device for detecting setting signals of the setting device; a device for outputting speech signals; an evaluation unit for receiving and evaluating the setting signals detected by the signal receiving device; and a device for generating speech signals in accordance with the evaluation signals of the evaluation unit; and by a method for dosing substances to be dispensed, in particular liquids, comprising the steps of: detecting a setting signal of a setting device; and outputting a speech signal in accordance with the setting signal detected.

In one embodiments, the present invention provides a device for delivering a substance comprising means for setting the amount of the substance to be delivered and producing setting signals, means for detecting the setting signals, means for receiving and evaluating the setting signals and producing evaluation signals, and means for generating speech signals in accordance with the evaluation signals.

The device in accordance with the invention for dosing substances to be dispensed, in particular liquids, such as is required for example when injecting insulin for diabetics and must be performed highly reliably, comprises a setting device, such as for example a rotating knob, using which the amount of the substance to be dispensed can be set. Furthermore, a signal receiving device is provided using which setting signals at the setting device can be detected. When using a rotating knob, this can be an increment provider which outputs a signal for each partial rotation, preferably between 1° and 180°, of the rotating knob. It is also possible to provide a "+" and a "−" key, wherein the duration or frequency for which the respective keys are operated is detected as setting signals. The signal receiving device outputs the detected setting signal or signals to an evaluation unit which determines a set dose or amount of the substance to be dispensed from said setting signals. In accordance with this determined dose, a control signal is output to a speech synthesizer which outputs a speech signal relating to the determined dose. This speech signal is transmitted to a speech output device, such as a loudspeaker or a hearing aid, such that a user of the device can hear which dose he has currently set. In some embodiments, this process is preferably continuous, such that a continuous speech output, or a speech output interrupted by short pauses, is possible even during the process of setting. This is particularly advantageous for blind or visually impaired users of the device in accordance with the invention, since they can easily verify the set dose, even during the process of setting, using the preferably constant speech output, and are not reliant on counting the number of rotations of a rotating knob during the process of setting. Further advantages follow from the fact that the user does not have to have visual contact with a setting device or a display, such that a desired dose can be set without the dosing device having to be held such that a display device arranged on it can be seen. Furthermore, no problems arise from an optical display becoming dirty, which can easily occur in the case of manually operating dosing devices, due to finger prints.

In one embodiments, a rotating knob is preferably provided as the setting device, wherein the amount of a substance to be dispensed is determined by the rotational angle and/or number of partial rotations of the rotating knob. For example, the rotational angle can be multiplied by a pre-set constant for determining the units to be dispensed per unit of angle. Furthermore, a locking device can be provided which audibly and/or tangibly locks the rotating knob after a completed rotational movement. Suitable locking devices be provided in such a way that they lock after a particular partial rotation, such a quarter-rotation or half-rotation, in order to enable fine tuning. Once locked, however, it should be possible to rotate the rotating knob further without significant force, such that while the rotating knob is tangibly or audibly locked, this does not obstruct setting. In general, however, a continuously rotating, non-locking rotating knob can also be used.

In one embodiment, the rotating knob is preferably formed such that a rotational movement of the knob is converted into an axial movement, which can be realized by using a suitable mechanism such as a screw mechanism. In this way, a substance to be dispensed can be directly dosed via the stroke of the rotating knob, said substance, once dosed, being dispensed or injected by means of a pressure force on the rotating knob. In the case of a dosing device designed in this way, the set amount is preferably output in accordance with the invention as a speech signal during and/or at the end of the process of setting.

However, the rotating knob can also be formed such that it is substantially not shifted axially when it is rotated, such that only signals corresponding to rotation are acted on, which can be used to control a dosing device, for example, an electric motor. The step of screwing the rotating knob back, for example, when a new ampoule is inserted, is thus omitted.

Furthermore, in some embodiments, it is possible to provide an increment provider as the signal receiving device on the rotating knob, said increment provider outputting a signal, for example an impulse signal, for each (partial) rotational movement of a pre-settable angle, and via this signal controlling a stepper motor by which the amount of a substance to be dispensed can be set. The signals output by the increment provider can also be directly routed to the evaluation unit, to be converted into a speech signal.

The embodiments of the invention mentioned above can be designed such that in a basic state, a particular settable offset is present, corresponding to the usual or average amount of the substance to be dispensed. This offset can either be set by the user, for example using the setting device itself, which can occur in a particular operation mode which can be selected by pressing the setting device, or by an additional rotatable device for setting a basic amount to be dispensed which can be increased or decreased by the user in accordance with the desired application, via the setting device. Furthermore, it is also possible for the user to read-in the offset amount of a substance to be dispensed in a different way, for example from a PC via an interface. Alternatively, it is possible for an offset to be pre-set by the manufacturer, the user then only having to modify the pre-set amount in accordance with the desired application. The use of an offset has the advantage, for example, in the case of dispensing insulin, that the user no longer has to set anything if an average amount of 24 units is dispensed. If, for example, before a large meal, it is desirable to dispense a greater amount, for example 28 units, then the user only has to perform the setting movements for four units, such that counting up to 28 during the process of setting is omitted, which makes the process significantly more simple and user-friendly. Since, in accordance with the invention, the set amount is output as speech, the use of an offset for the amount to be dispensed cannot result in the device being incorrectly set, since the amount set as the offset can also be output as a speech output, such as "twenty-four", during the process of setting, wherein each alteration to the basic amount pre-set by an offset can likewise be output as a speech signal, such as a continuous count of "twenty-five, twenty-six, . . . ", while the setting device is operated.

In some embodiments, an operating device is preferably provided that can be informed that the values or signals output via the speech output device have been understood by the user, that dispensing the substance is to be prepared or performed or that an operational mode is being changed. A key or a microphone can, for example, be provided as the operating device, into which a defined speech signal, such as "understood" can be spoken, such that a repeated speech output of a set amount is interrupted and dispensing the set amount can be enabled. It is also possible to operate the input device itself in a way other than for setting the dose. A rotating knob could, for example, be pressed if setting is complete.

In some embodiments, a device for outputting an alarm or warning signal, which can also be integrated in the evaluation unit, is preferably provided, to output a warning signal to the user when unusual amounts, such as an exceedingly small or excessively large dose, is set. The warning signal may be a speech output, which can be a general warning message to the user, such as "warning! verify amount set!", or a specific speech output in accordance with the unusual setting detected, such as "set amount too large!". It is in general conceivable to provide different specific speech output signals in accordance with different states of the dosing device in accordance with the invention. Optical or tangible and/or audible warning signals can also be output when unusual settings are detected. Furthermore, combinations of different warning signals are also possible, to indicate amounts which are probably incorrectly set. The dosing device in accordance with the invention can also be designed such that particular limits for the maximum amount to be dispensed can be set, which ensure that a dangerous dose cannot be dispensed if the device is incorrectly operated.

The speech output device can also be formed such that it does not output directly audible speech, as in the case of a loudspeaker, but rather corresponding signals are output from the device in accordance with the invention, which are only then converted into audible speech signals by another device. In this way, a connector for an earpiece which can be plugged in or a coupling for a hearing aid can be provided, wherein the output signals can be transmitted to the hearing aid by radio. Thus, it is not necessary for there to be a physical connection between the dosing device and the hearing aid, making setting significantly easier.

In some embodiments, it may be advantageous to provide a device for modifying the volume, particular frequency ranges or other characteristics of the speech signal to be output, such that, for example, low tones which are heard less well by a particular user can be amplified. Furthermore, it is conceivable to alter the contents of the speech signal to be output via the modifying device. For example, it is conceivable to provide an output of speech signals in different languages or for different operational modes of the dosing device in accordance with the invention.

In addition to the speech output device, in some embodiments, one or more output devices are preferably provided, such as an optical display, a device outputting a tangible or tactile signal, such as a vibrating element, an interface which can output information on the amount set, the time a substance is dispensed or similar values, or other suitable output device. In this way, for example, a record of the amounts dispensed, together with the corresponding times of day in each case, can be output to an external device, in order to store appropriate information in an electronic diary of the user of the device in accordance with the invention, such that a physician can obtain an overview of the amounts of insulin injected. Furthermore, in some embodiments, it is possible for data to be input into the device in accordance with the invention via an interface provided on the dosing device, in order to read in an average value as an offset for setting the amount to be dispensed on average, or to program the speech output device to a desired language and/or to read-in desired speech output signals into it.

Advantageously, in some embodiments, the dosing device in accordance with the invention can be configured such that an amount set is output as a speech signal a number of times, such that, for example, when 24 units are set the word "twenty-four" is output three times if no alteration by the setting device is detected after a settable period of time, before the speech output is switched off. The speech output can then immediately be re-activated if a setting operation by the user is detected. By outputting a set final value three times, for example, the user can be informed that this final value for dosing the substance to be dispensed has been permanently set and has not been inadvertently altered by unintentionally operating the setting device. Furthermore, it is possible to configure the dosing device such that other parameters of interest to the user can be output, in accordance with an operational mode set, such as the remaining amount of the substance to be dispensed present in the dosing device, the total amount previously dispensed, the dose of the last dispensed amount, the operational state such as error messages in particular parts, an indication that only a little substance to be dispensed is left in the dosing device, or the like. To this end, suitable selecting devices for setting the operational mode, such as operating keys or speech input systems, can be provided.

In some embodiments, in accordance with the invention, the method for dosing substances to be dispensed comprises the following steps: detecting the operation or alteration of a setting device for dosing the substance to be dispensed, wherein information on the amount set is preferably output continuously as a speech output, in accordance with this detected setting signal.

In some embodiments, it is possible that only the final value of a dosing amount set is output as a speech output. However, there is preferably a speech output during the entire process of setting, i.e., for example the number of units to be dispensed set is output continuously or at short time intervals of 1 to 5 seconds, or there is a speech output for each alteration to the amount to be dispensed set, such that the user can hear a continuous count of the setting amount. This design is highly advantageous for a user, since he is continuously informed about the amount set during a process of setting, so cannot miscount during a process of setting while rotating a setting knob relating to the rotational movements carried out. Setting can thus be interactive and, in some embodiments, can be completed by pressing the rotating knob.

In some embodiments, warning signals and/or operational instructions are preferably output to the user, which need not necessarily be only during a process of setting, in order to inform the user about particular operational states, such as the need to re-charge a battery pack, insert a new ampoule into the dosing device, or re-verify the amount set because it seems unusual, or to instruct the user that a new injection should be performed shortly. In general, any desired operational states or user information can be output to the user as a speech output.

BRIEF DESCRIPTION OF THE DRAWINGS

The invention will now be described by way of an exemplary embodiment and by referring to the accompanying figures.

FIG. 1 depicts an exemplary embodiment of the device in accordance with the invention; and FIG. 2 is a flow diagram illustrating one embodiment of the method in accordance with the invention.

DETAILED DESCRIPTION

FIG. 1 shows a device in accordance with the invention for dosing substances to be dispensed, in particular liquids, wherein for the sake of simplification, only the rear part of a so-called pen pump 10 is shown. In general, however, the invention can be used with any pumps, so-called pens, or with any other devices in which a substance to be dispensed, which could also be a cream or a gel, is to be dosed as exactly as possible.

In one embodiments, on the left end (as shown) of the dosing device 10 in accordance with the invention, a rotating knob 1 is provided which comprises axially running grooves 1a about its circumference, distributed at equal intervals. These grooves 1a can lock with locking devices 1b, adjacent to the circumference of the rotating knob 1 and distributed about the circumference of the rotating knob 1a, wherein a locking device 1b, such as an elastic or other suitable element, which locks into a groove 1a, can be released again by applying a measurable force which is as small as possible. At least one signal receiving device 2 is arranged, distributed in the circumferential direction about the rotating knob 1, said signal receiving device being an increment provider and outputting a signal to an integrated circuit 3 when it passes a groove 1a. Codings can also be provided on the rotating knob 1 which enable the rotational movement and rotational direction of the rotating knob 1 to be detected as continuously as possible. In the embodiment shown, the rotating knob 1 is not formed as a screw rotating knob, such that it does not move in the axial direction when there is a rotational movement. However, it is also conceivable to use a rotating knob 1 which can be screwed in and out, in order to then act directly on an ampoule containing a substance to be dispensed.

The signals relating to the setting position of the rotational knob 1, detected by the increment provider 2 shown in FIG. 1, are evaluated in the integrated circuit 3 and converted into speech signals which are output via a connected loudspeaker 4, in order to output acoustic or speech signals to a user, relating to the amount set. Furthermore, the information relating to the amount set is output via a signal line 5 to a step motor or other suitable dosing device, immediately or only after the process of setting is complete, said dosing device preparing the amount of the substance to be dispensed. The substance to be dispensed can be pumped from a storage container, such as an ampoule, into an injection space, from which the substance is dispensed outwards in an injection. Dosing substances to be dispensed by means of suitable devices is known in the prior art and will correspondingly not be discussed in more detail here.

FIG. 2 shows a flow diagram of one embodiments of the method in accordance with the invention, for dosing substances to be dispensed, wherein in the embodiment shown in FIG. 1, the rotational movement of the dosing knob 1 is detected in a first step. The detected rotational movement is converted into pre-set units which can be displayed on a 7-segment display, as is known in the prior art. The value "24" is shown in FIG. 2 by way of example. In accordance with the invention, the setting signals are converted into speech signals by means of suitable speech synthesizing and output as speech, such as outputting the word "twenty-four" as shown in FIG. 2.

Any components and materials for use in and for forming or fabricating the device of the present invention, including any electrical components, circuitry, wires, connections, circuit boards or microprocessors, and control system components, are intended to be conventional, commercially available components unless otherwise indicated. Further, it is possible that those skilled in the state of the art will be able to recognize and select equivalent items.

In the foregoing description, embodiments of the present invention, including preferred embodiments, have been presented for the purpose of illustration and description. It is not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for dosing medicinal substances to be dispensed, comprising the steps of:
   a) detecting a setting signal of a setting device capable of altering and confirming a pre-set offset dosage;
   b) outputting a speech signal in accordance with the setting signal detected wherein the output speech signal is a specific dosage number;
   c) detecting a confirmation signal of the setting device corresponding to user confirmation that the speech signal was understood.

2. The method as set forth in claim 1, wherein said substances to be dispensed are liquids.

3. The method as set forth in claim 1, wherein a speech signal is output one of continuously or at particular time intervals during a process of setting.

4. The method as set forth in claim 1, wherein an information or warning signal is output when an operational state occurs.

5. A device for delivering a medicinal substance, comprising:
   means for setting the amount of the substance to be delivered and producing setting signals, wherein the means for setting is capable of altering and confirming a pre-set offset dosage;
   means for detecting the setting signals;
   means for receiving and evaluating the setting signals and producing evaluation signals;
   means for generating speech signals in accordance with the evaluation signals wherein the generated speech signals are a specific dosage number; and
   means for detecting a confirmation signal corresponding to user confirmation that the generated speech signals were understood.

6. A device for dosing medicinal substances to be dispensed, comprising:
   a) a setting device for setting the amount of the substance to be dispensed and producing setting signals, wherein the setting device is capable of altering and confirming a pre-set offset dosage;
   b) a signal receiving device for detecting the setting signals of said setting device; and
   c) a device for outputting speech signals comprising:
      an evaluation unit for receiving and evaluating said setting signals detected by said signal receiving device; and
      a device for generating speech signals in accordance with the evaluation signals of said evaluation unit, the device being configured to recite a specific dosage number in speech form;
   wherein the signal receiving device detects confirmation signals confirming the speech signals were understood.

7. The device as set forth in claim 6, wherein said substances to be dispensed are liquids.

8. The device as set forth in claim 6, wherein said substances to be dispensed are dosed for an injection.

9. The device as set forth in claim 6, wherein the setting device is a rotating knob.

10. The device as set forth in claim 9, wherein said rotating knob is a locking rotating knob.

11. The device as set forth in claim 9, wherein said rotating knob can be adjusted axially with respect to its rotational direction.

12. The device as set forth in claim 9, wherein the rotating knob substantially cannot be altered in the axial direction.

13. The device as set forth in claim 6, further comprising an input device for inputting user signals.

14. The device as set forth in claim 13, wherein said input device comprises a switch and a microphone.

15. The device as set forth in claim 13, wherein the setting device comprises said input device.

16. The device as set forth in claim 6, further comprising a warning device for outputting a warning signal.

17. The device as set forth in claim 6, wherein said speech output device is one of a loudspeaker, an electrical plug connection for connecting a loudspeaker, or a transmitting device.

18. The device as set forth in claim 6, further comprising a device for modifying the speech signals generated.

19. The device as set forth in claim 6, further comprising an output device which produces optical or tactile signals.

20. The device as set forth in claim 6, further comprising a PC interface for inputting and/or outputting data to or from said dosing device.

21. The device as set forth in claim 6, wherein the offset dosage is set by a user of the device.

22. The device as set forth in claim 6, wherein the offset dosage is pre-set by a manufacturer of the device.

23. The device as set forth in claim 6, wherein the offset dosage is set from a PC via an interface.

24. A device for dosing substances to be dispensed, comprising:
   a) a rotating knob for setting the amount of the substance to be dispensed, said rotating knob comprising one or more elements on an outer circumference of said rotating knob for producing setting signals;
   b) a signal receiving device for detecting the setting signals produced by said rotating knob, said signals produced upon said one of said one or more elements passing a portion of said signal receiving device;
   c) a device for outputting speech signals comprising:
      an integrated circuit for receiving and evaluating said setting signals detected by said signal receiving device; and
      a device for generating speech signals in accordance with the evaluation signals of said evaluation unit, the device being configured to recite a specific dosage number in speech form; and
   d) wherein said integrated circuit is further configured to receive input signals corresponding to user confirmation that the speech signals generated were understood.

25. The device as set forth in claim 24, wherein the input signals comprise signals corresponding to a movement that depresses said rotating knob.

26. The device as set forth in claim 24, wherein the input signals comprise speech signals, said speech signals corresponding to speech of the user of the device.

27. The device as set forth in claim 24, wherein the integrated circuit is further configured to operate said device for outputting speech signals in a plurality of operating modes, each of said plurality of operating modes relating to a parameter of interest of said device, said operating modes selectable by a user.

28. The device according to claim 27, wherein the operating mode is selectable via one or more operating keys arranged on said device.

29. The device according to claim 27, wherein the operating mode is selectable via speech input received from a microphone communicatively coupled to said device.

* * * * *

UNITED STATES PATENT AND TRADEMARK OFFICE
CERTIFICATE OF CORRECTION

PATENT NO. : 7,201,741 B2 Page 1 of 1
APPLICATION NO. : 10/360190
DATED : April 10, 2007
INVENTOR(S) : Bruno Maire It is certified that error appears in the above-identified patent and that said Letters Patent is hereby corrected as shown below:

Specification:

| Col. | Line | PTO | Should Read |
|---|---|---|---|
| 1 | 60 | "In one embodiments" | -- In one embodiment, -- |
| 2 | 40 | "In one embodiments" | -- In one embodiment, -- |
| 6 | 1 | "In one embodiments" | -- In one embodiment, -- |
| 6 | 41 | "of one embodiments" | -- of one embodiment -- |

Claims:

| Col. | Line | PTO | Should Read |
|---|---|---|---|
| 7 | 16 | "number" | -- number; and -- |

Signed and Sealed this

Seventh Day of August, 2007

JON W. DUDAS
*Director of the United States Patent and Trademark Office*